United States Patent
MacDougall et al.

(10) Patent No.: US 9,572,488 B2
(45) Date of Patent: Feb. 21, 2017

(54) HEAD MOUNTABLE DEVICE FOR MEASURING EYE MOVEMENT

(71) Applicant: GN Otometrics A/S, Taastrup (DK)

(72) Inventors: Hamish MacDougall, Woolloomooloo (AU); Konrad P. Weber, Zurich (CH); Anders Thøsing Andersen, Lille Skensved (DK); Izaak Kopilewicz, Brønshøj (DK)

(73) Assignee: GN OTOMETRICS A/S, Taastrup (DK)

( * ) Notice: Subject to any disclaimer, the term of this patent is extended or adjusted under 35 U.S.C. 154(b) by 0 days.

(21) Appl. No.: 14/496,435

(22) Filed: Sep. 25, 2014

(65) Prior Publication Data

US 2016/0081546 A1 Mar. 24, 2016

(30) Foreign Application Priority Data

Sep. 23, 2014 (DK) ................................. 2014 70584
Sep. 23, 2014 (EP) ..................................... 14185921

(51) Int. Cl.
*A61B 3/14* (2006.01)
*A61B 3/113* (2006.01)
*A61B 3/00* (2006.01)

(52) U.S. Cl.
CPC .............. *A61B 3/113* (2013.01); *A61B 3/0025* (2013.01); *A61B 3/0058* (2013.01); *A61B 3/145* (2013.01)

(58) Field of Classification Search
CPC .............. G02B 27/017; G02B 27/0093; G02B 2027/0178; G02B 2027/014; G02B 2027/0138

USPC ................................................... 351/209, 210
See application file for complete search history.

(56) References Cited

U.S. PATENT DOCUMENTS

| | | | |
|---|---|---|---|
| 4,509,081 A | 4/1985 | Peyton et al. | |
| 5,094,521 A | 3/1992 | Jolson et al. | |
| 5,751,258 A * | 5/1998 | Fergason | A61F 9/067 345/7 |
| 5,821,989 A | 10/1998 | Lazzaro et al. | |
| 5,838,420 A | 11/1998 | MacGregor Donaldson | |
| 6,414,681 B1 | 7/2002 | Ohshima | |
| 2004/0181168 A1 | 9/2004 | Plant et al. | |
| 2007/0017534 A1 | 1/2007 | Thorpe | |
| 2010/0110368 A1 | 5/2010 | Chaum | |

OTHER PUBLICATIONS

Extended European Search Report dated Mar. 11, 2015, for corresponding European Patent Application No. 14185921.5, 11 pages.

(Continued)

*Primary Examiner* — Mahidere Sahle
(74) *Attorney, Agent, or Firm* — Vista IP Law Group, LLP

(57) ABSTRACT

A head mountable device for measuring eye movement includes: a frame; a camera system comprising a first camera, wherein the camera system is coupled to the frame, and is configured to obtain a first set of images of a first eye of a user; and a first liquid crystal display (LCD) shutter configured to control passage of light to the first eye based at least in part on a first control signal, the first LCD shutter is configured to operate in a first primary mode and a first secondary mode, wherein the first LCD shutter is configured to allow less light to reach the first eye in the first secondary mode than in the first primary mode.

16 Claims, 10 Drawing Sheets

(56) References Cited

OTHER PUBLICATIONS

A. H. Clarke et al., "Using high frame rate CMOS sensors for three-dimensional eye tracking", Behavior Research Methods, Instruments, & Computers : a journal of the Psychonomic Society, Inc., Nov. 1, 2002, pp. 549-560, XP055136469, 12 pages.
First Technical Examination and Search Report dated Apr. 20, 2015, for corresponding Danish Patent Application No. PA 2014 70584, 6 pages.

\* cited by examiner

HEAD MOUNTABLE DEVICE FOR MEASURING EYE MOVEMENT

RELATED APPLICATION DATA

This application claims priority to and the benefit of Danish Patent Application No. PA 2014 70584 filed on Sep. 23, 2014, pending, and European Patent Application No. 14185921.5 filed on Sep. 23, 2014. The entire disclosures of both of the above applications are expressly incorporated by reference in their entireties herein.

FIELD

The present disclosure relates to a device for measuring eye movement, in particular a head mountable device for measuring eye movement in relation to tests involving deprivation of sight of one or more of the eyes of a user. Such tests may be ophthalmologic, vestibular, and/or neurologic tests.

BACKGROUND

There is an ongoing investigation towards developing measurement techniques and equipment for measuring eye movement of humans. Various ophthalmologic, vestibular and neurologic tests exists which involves observing eye movements. Tests may comprise observation of eye movements during concurrent sight deprivation of either one eye or both eyes. Tests incorporating deprivation of sight of either one or both eyes may comprise HINTS tests, or individual parts of the HINTS tests, such as test of skew and/or tests of nystagmus.

Tests may comprise measuring fast eye movements, e.g. eye saccades, lasting approximately between 20-200 ms and involving angular speed up to 900 deg/s. Such fast movements may be visual to the clinician, but may be difficult to quantify consistently. Tests may comprise measuring very small eye deviations, e.g. skew, which may be difficult to detect and/or quantify subjectively.

It is desirable to circumvent subjective measurements and provide a possible standardized test, which is independent of the clinician or other person performing the test. Furthermore, in some environments, such as in pre hospital settings, it may be problematic, if not impossible, to accurately perform the test when relying on subjective measurements.

Furthermore, sight deprivation is conventionally performed by placing a black cover over the patient's eye. The cover may be a hard plastic or the hand of the clinician. Some devices may comprise a black cover, such as a visor, which is able to be lowered over the patient's eyes. However, it is desirable that a device capable of performing the above mentioned tests is able to control the deprivation of sight in an accurate, consistent, secure, comfortable, and easy way.

SUMMARY

There is a need for an improved device which avoids the use of subjective measures in ophthalmologic, vestibular, and/or neurologic tests, and which avoid or limits the need of user interaction during tests, and hence is able to reliably measure eye movement when performing various tests. The present disclosure provides a device and a method which provides objective and reproducible measurement of eye movement in tests requiring deprivation of sight.

Disclosed is a head mountable device for measuring eye movement. The head mountable device comprises a frame, a camera system, and a first liquid crystal display (LCD) shutter. The camera system comprises a first camera, wherein the camera system is configured to obtain a first set of images of a first eye of a user. The first LCD shutter is configured to control passage of light to at least part of the first eye based on a first control signal. The first LCD shutter is configured to operate in a first primary mode and a first secondary mode, where passage of light through the first LCD shutter in the first secondary mode is restricted relative to the first primary mode.

Also disclosed is a method for measuring eye movement of a user using a head mountable device, such as the disclosed head mountable device, comprising a frame, a camera system comprising a first camera, and a first liquid crystal display (LCD) shutter configured to control passage of light to at least part of a first eye of a user based on a first control signal. The first LCD shutter is configured to operate in a first primary mode and a first secondary mode, where passage of light through the first LCD shutter in the first secondary mode is restricted relative to the first primary mode. The method comprising: adjusting passage of light to at least part of the first eye by operation of the first LCD shutter; and obtaining a first set of images of the first eye by the camera system.

The method may be implemented with the device for measuring eye movement. At least a part of the method may be incorporated in software adapted to run in a processing unit, such as a processing unit of the device for measuring eye movement.

It is envisaged that any embodiments or elements as described in connection with any one aspect may be used with any other aspects or embodiments, mutatis mutandis.

The method and apparatus as disclosed enables fast and objective examination of ophthalmologic, vestibular and neurologic parameters. Objective examinations as an alternative to conventional subjective assessments may provide more reliable and consistent examinations. Hence, incorrect or unnecessary treatment may be avoided, and improved possibility of detecting changes in a patient's condition is provided. Furthermore, the disclosed method and apparatus provides automatically controlled sight deprivation, which enables automation and standardization of tests requiring sight deprivation, and/or limits the need for a clinician's interaction during the test. Furthermore, electronic control of the sight deprivation improves the accuracy and precision of measurements.

The head mountable device comprises a frame. The frame may be configured to be fixated to the head of the user, e.g. by adjustable and/or elastic straps. The frame may be in the form a goggle, a helmet, a cap, and/or another head mountable equipment. In an embodiment, the frame is embodied as a goggle. The frame may be configured to fasten the head mountable device to the head of the user such as to prevent motion of the head mountable device relative to the head of the user. The frame may accommodate elements of the head mountable device. The frame may accommodate the camera system and/or the first LCD shutter. The camera system and/or the first LCD shutter may be attached to the frame.

The method may further comprise mounting the head mountable device and/or the frame to the head of the user.

The head mountable device may be operable without attached wires. The head mountable device may comprise a power supply, such as a battery power supply and/or a power inlet. The frame may accommodate power supply. The power supply may be attached to the frame. Providing a power supply may allow operation of the head mountable device without the need of a power outlet, thus providing an increased scope of operation, e.g. the head mountable device may be used in an ambulance or at an accident site.

The head mountable device may be configured to control passage of light to at least part of a second eye of the user. For example, the first LCD shutter may additionally be configured to control passage of light to at least a part of the second eye. Alternatively and/or additionally, the head mountable device may comprise a second liquid crystal display (LCD) shutter configured to control passage of light to at least part of the second eye of the user based on a second control signal. The second LCD shutter may be configured to operate in a second primary mode and a second secondary mode, where passage of light through the second LCD shutter in the second secondary mode is restricted relative to the second primary mode. The frame may accommodate the second LCD shutter.

The first LCD shutter may be configured to allow less light to reach the first eye in the first secondary mode than in the first primary mode.

The second LCD shutter may be configured to allow less light to reach the second eye in the second secondary mode than in the second primary mode.

Passage of light through the first LCD shutter in the first primary mode, and/or passage of light though the second LCD shutter in the second primary mode, may be configured to allow passage of a certain amount of light. Passage of light through the first LCD shutter in the first primary mode, and/or passage of light though the second LCD shutter in the second primary mode, may be restricted relative to complete passage of light. For example, passage of light through the first LCD shutter in the first primary mode, and/or passage of light though the second LCD shutter in the second primary mode, may be restricted to less than 90% of the light reaching the respective first and/or second LCD shutter, or less than 85% of the light reaching the respective first and/or second LCD shutter, or less than 70% of the light reaching the respective first and/or second LCD shutter, or less than 50% of the light reaching the respective first and/or second LCD shutter, or less than 30% of the light reaching the respective first and/or second LCD shutter.

Passage of light through the first LCD shutter in the first secondary mode, and/or passage of light though the second LCD shutter in the second secondary mode, may be configured to block passage of light. For example, passage of light through the first LCD shutter in the first secondary mode, and/or passage of light though the second LCD shutter in the second secondary mode, may be restricted to less than 5% of the light reaching the respective first and/or second LCD shutter, or less than 10% of the light reaching the respective first and/or second LCD shutter, or less than 20% of the light reaching the respective first and/or second LCD shutter, or less than 35% of the light reaching the respective first and/or second LCD shutter, or less than 50% of the light reaching the respective first and/or second LCD shutter.

A common control signal may control passage of light through the first and/or second LCD shutter. The first LCD shutter may be configured to control passage of light through the first LCD shutter based on the first control signal and the common control signal. The second LCD shutter may be configured to control passage of light through the second LCD shutter based on the second control signal and the common control signal. For example, passage of light through the first LCD shutter and/or the second LCD shutter may be controlled by a phase difference between the common control signal and the first control signal and/or second control signal, respectively.

For example, the first control signal and the common control signal being out of phase, such as 180 degrees out of phase, or between 90 and 180 degrees out of phase, or having a phase difference of more than 90 degrees, may result in the first LCD shutter operating in the first secondary operating mode where passage of light through the first LCD shutter is restricted and/or blocked relative to the first primary operating mode. The first control signal and the common control signal being in phase, or having a phase difference of less than 90 degrees, may result in the first LCD shutter operating in the first primary operating mode where passage of light through the first LCD shutter is at least less restricted and/or blocked relative to the first secondary operating mode.

Additionally and/or alternatively, the second control signal and the common control signal being out of phase, such as 180 degrees out of phase, or between 90 and 180 degrees out of phase, or having a phase difference of more than 90 degrees, may result in the second LCD shutter operating in the second secondary operating mode where passage of light through the second LCD shutter is restricted and/or blocked relative to the second primary operating mode. The second control signal and the common control signal being in phase, or having a phase difference of less than 90 degrees, may result in the second LCD shutter operating in the second primary operating mode where passage of light through the second LCD shutter is at least less restricted and/or blocked relative to the second secondary operating mode.

The control signals, such as the first control signal, the second control signal, and/or the common control signal, may be any types of signal, e.g. direct current (DC) and/or alternating current (AC) voltage signals. For example, the first control signal, the second control signal, and/or the common control signal may be alternating current (AC) signal(s). The first control signal, the second control signal, and/or the common control signal may be bipolar square wave voltage signal(s). It may be desirable to use a signal with an alternating component, such as AC signals and/or square wave signals, as this may prevent migration of crystals in the first and/or second LCD shutter(s), thereby decreasing the risk of damage to the first and/or second LCD shutter(s).

The voltage of the control signals, such as the first control signal, the second control signal, and/or the common control signal, may be chosen according to a specification of the LCD shutter(s). The voltage of the first control signal, the second control signal, and/or the common control signal may be in the range from 2 to 14 volts, such as 5 volts or such as 10 volts. The voltage difference between the first and/or second control signal(s) and the common control signal may be in the range from 2 to 14 volts, such as 5 volts or such as 10 volts.

In some tests, it may be beneficial to be able to obtain images of both eyes of a user. Hence, the camera system may be configured to obtain a second set of images of a second eye of the user. The first camera may be configured to obtain the first set of images and the second set of images. Alternatively and/or additionally, the camera system may comprise a second camera configured to obtain the second set of images.

The first set of images may be configured to be obtained with a first frame rate. The first frame rate may be selected such as to enable detection of eye saccades of the first eye. The second set of images may be configured to be obtained with a second frame rate. The second frame rate may be selected such as to enable detection of eye saccades of the second eye. The first frame rate and the second frame rate may be the same frame rate.

Obtaining the first set of images and/or the second set of images preferably enable detection of eye saccades of the first eye and/or of the second eye. Eye saccades may be very fast, e.g. eye saccades may last for only 20 ms. Therefore, the first frame rate and/or the second frame rate may be sufficiently high to enable reliable detection of eye saccades. For example, the first frame rate and/or the second frame rate may be higher than 125 frames per second (fps), such as higher than 150 fps, such as higher than 175 fps, such as higher than 200 fps, such as 250 fps. In other examples, the first frame rate and/or the second frame rate may be less than 125 fps, but is still sufficiently high to allow the processing unit to detect eye saccades of the first eye and/or of the second eye.

The head mountable device may comprise a first mirror for mirroring images of the first eye towards the first camera, and/or for mirroring images of the first eye towards the second camera, and/or for mirroring images of the second eye towards the first camera, and/or for mirroring images of the second eye towards the second camera. Additionally, the head mountable device may comprise a second mirror for mirroring images of the second eye towards the first camera and/or for mirroring images of the second eye towards the second camera.

The frame may accommodate the first mirror and/or the second mirror.

The first camera and/or the second camera may be focused on the first and/or second eye. The first camera and/or the second camera may be focused on the first and/or second eye, respectively, via the first and/or second mirror, respectively.

The head mountable device may comprise a first light source for emitting first electromagnetic radiation towards the first eye and/or the second eye. The first mirror and/or the second mirror may be configured to direct at least a part of the first electromagnetic radiation towards the first eye and/or the second eye.

The head mountable device may comprise a second light source for emitting second electromagnetic radiation towards the first and/or second eye. The first mirror and/or the second mirror may be configured to direct at least a part of the second electromagnetic radiation towards the first eye and/or the second eye.

The frame may accommodate the first light source and/or the second light source.

The first and/or second electromagnetic radiation may comprise infrared radiation, laser radiation, visible red radiation, visible blue radiation, visible green radiation, and/or visible orange radiation. The first and/or second electromagnetic radiation may comprise electromagnetic radiation with wavelengths in the range of 380-450 nm, or in the range of 450-495 nm, or in the range of 495-570 nm, or in the range of 570-590 nm, or in the range of 590-620 nm, or in the range of 620-750 nm, or in the range of 750-2.500 nm, or in the range of 2.500-10.000 nm, or in the range of 10.000-1.000.000 nm.

The first and/or second light source may be used for testing the first and/or second eye's response to light. The first and/or second light source may be used to light up the first and/or second eye. The first and/or second light source may be used to light up the first and/or second eye for the camera system to obtain images of the first and/or second eye.

The camera system and/or the first camera and/or the second camera may be configured to detect the first electromagnetic radiation and/or the second electromagnetic radiation.

The first and/or second mirror may be partly transparent. For example, the first and/or second mirror may be transparent to one or more selected ranges of electromagnetic radiation. The first and/or second mirror may be transparent to visible light, such as electromagnetic radiation with wavelengths in the range of 380-750 nm.

The first LCD shutter and/or the second LCD shutter may be configured to control passage of light with wavelengths of the first and/or second electromagnetic radiation.

The first LCD shutter and/or the second LCD shutter may be configured to allow passage of light with wavelengths of the first and/or second electromagnetic radiation. The first LCD shutter and/or the second LCD shutter may be configured to control passage of light with wavelengths different than the first and/or second electromagnetic radiation. For example, the first LCD shutter allows passage of infrared light in the first secondary mode, while passage of visible light through the first LCD shutter in the first secondary mode is restricted relative to the first primary mode. Additionally or in an alternative example, the second LCD shutter allows passage of infrared light in the second secondary mode, while passage of visible light through the second LCD shutter in the second secondary mode is restricted relative to the second primary mode.

The first LCD shutter may comprise a first polarizer having a first polarization. The second LCD shutter may comprise a second polarizer having a second polarization. The first polarization may be different than the second polarization, e.g. the first polarization may be 90 degrees rotated relative to the second polarization.

The head mountable device may comprise one or more processing unit(s), such as a first processing unit and/or a second processing unit.

The head mountable device may comprise a processing unit, such as the first processing unit, configured to control the first LCD shutter and/or the second LCD shutter. The first control signal, the second control signal, and/or the common control signal may be controlled by the first processing unit.

The head mountable device may comprise a processing unit, such as the first processing unit or a second processing unit, configured to process the first set of images and/or the second set of images. The processing unit, e.g. the first processing unit and/or the second processing unit, may be configured to provide a processing unit output based on the first set of images and/or the second set of images.

The processing unit configured to process the first set of images may be the same processing unit as the processing unit configured to control the first LCD shutter and/or the second LCD shutter. For example, the first processing unit may be configured to process the first set of images and/or the second set of images and provide a processing unit output based on the first set of images and/or the second set of images, and the first control signal, the second control signal, and/or the common control signal may be controlled by the first processing unit.

The frame may accommodate the processing unit, such as the first processing unit and/or the second processing unit.

The head mountable device may comprise an interface for providing a device output based on the first set of images and/or the second set of images. The method may comprise providing a device output based on the first set of images and/or the second set of images. The interface may comprise one or more types of interfaces for providing the device output to a user and/or an operator of the head mountable device.

The frame may accommodate the interface.

The interface may comprise one or more display(s), such as a first display and/or a second display. The one or more display(s), such as the first display and/or the second display, may be an organic light emitting diode (OLED), an OLED display, a light emitting diode (LED), an LED display, and/or an e-ink display. The one or more display(s), such as the first display and/or the second display, may visually provide the device output, or part of the device output, to a user or an operator. The device output may comprise a visual output.

The interface may comprise one or more speaker(s), such as a first speaker and/or a second speaker. The one or more speaker(s), such as the first speaker and/or the second speaker, may audiologically provide the device output, or part of the device output, to a user or an operator. The device output may comprise an audiologic output.

The interface may comprise one or more wireless transmitter unit(s). The interface may comprise a wireless transceiver unit comprising the wireless transmitter unit and a wireless receiver unit. The wireless transmitter unit and/or the wireless transceiver unit and/or the wireless receiver unit may operate according to Bluetooth, WiFi, 3G, and/or 4G.

Providing the device output may comprise transmitting the device output wirelessly to an external display. The wireless transmitter unit may be configured to transmit the device output, or a part of the device output, to a display, such as an external display. The external display may be external to the head mountable device. The external display may be external to the frame of the head mountable device. The external display may be a display of a smartphone, a tablet computer, a laptop, a TV, a smart-TV, and/or the like.

The interface may comprise an input device for enabling control of the head mountable device, such as enabling control of the first LCD shutter and/or the second LCD shutter. The input device may enable control of the first LCD shutter and/or the second LCD shutter via control of the processing unit, such as the first processing unit. The input device may be the wireless receiver. Alternatively or additionally, the input device may comprise a touch display, a push button and/or a switch.

The head mountable device may comprise additional measurement units. For example, the head mountable device may comprise a motion sensor configured to detect movement of the head mountable device. The frame may accommodate the additional measurement units, such as the motion sensor. The motion sensor may comprise one or more gyroscope(s) and/or one or more accelerometer(s) and/or one or more camera(s). Additional measurement units may provide additional uses of the head mountable device, e.g. the head mountable device may be configurable to be used in more tests.

The frame may accommodate any or all of the above mentioned elements. Hence, the head mountable device may be configured as a standalone device without the need for external connections.

A head mountable device for measuring eye movement includes: a frame; a camera system comprising a first camera, wherein the camera system is coupled to the frame, and is configured to obtain a first set of images of a first eye of a user; and a first liquid crystal display (LCD) shutter configured to control passage of light to the first eye based at least in part on a first control signal, the first LCD shutter is configured to operate in a first primary mode and a first secondary mode, wherein the first LCD shutter is configured to allow less light to reach the first eye in the first secondary mode than in the first primary mode.

Optionally, the head mountable device further includes a first mirror for mirroring images of the first eye towards the first camera.

Optionally, the head mountable device further includes a second liquid crystal display (LCD) shutter configured to control passage of light to a second eye of the user based at least in part on a second control signal, the second LCD shutter being configured to operate in a second primary mode and a second secondary mode, wherein the second LCD shutter is configured to allow less light to reach the second eye in the second secondary mode than in the second primary mode.

Optionally, the first LCD shutter is configured to control passage of light through the first LCD shutter based on the first control signal and a common control signal, and wherein the second LCD shutter is configured to control passage of light through the second LCD shutter based on the second control signal and the common control signal.

Optionally, the first control signal, the second control signal, and/or the common control signal comprises alternating current (AC) signal(s) and/or bipolar square wave voltage signal(s).

Optionally, a voltage of at least one of the first control signal, the second control signal, and the common control signal is anywhere from 2 to 14 volts.

Optionally, the camera system is configured to obtain a second set of images of a second eye of the user.

Optionally, the camera system comprises a second camera configured to obtain the second set of images.

Optionally, the camera system is configured to obtain the first set of images with a first frame rate, the first frame rate being sufficient to enable detection of eye saccades of the first eye.

Optionally, the head mountable device further includes a processing unit configured to process the first set of images and to provide a processing unit output based on the first set of images.

Optionally, the first control signal is controlled by the processing unit.

Optionally, the head mountable device further includes an interface for providing a device output based on the first set of images.

Optionally, the frame accommodates the camera system and the first LCD shutter.

A method performed by a head mountable device, the head mountable device comprising a frame, a camera system coupled to the frame and comprising a first camera, and a first liquid crystal display (LCD) shutter configured to control passage of light to a first eye of a user based at least in part on a first control signal, the first LCD shutter being configured to operate in a first primary mode and a first secondary mode, wherein the first LCD shutter is configured to allow less light to reach the first eye in the first secondary mode than in the first primary mode, the method includes: adjusting passage of light to the first eye by operation of the first LCD shutter; and obtaining a first set of images of the first eye by the camera system.

Optionally, the method further includes providing a device output based on the first set of images.

Other features and advantages will be described below in the detailed description.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
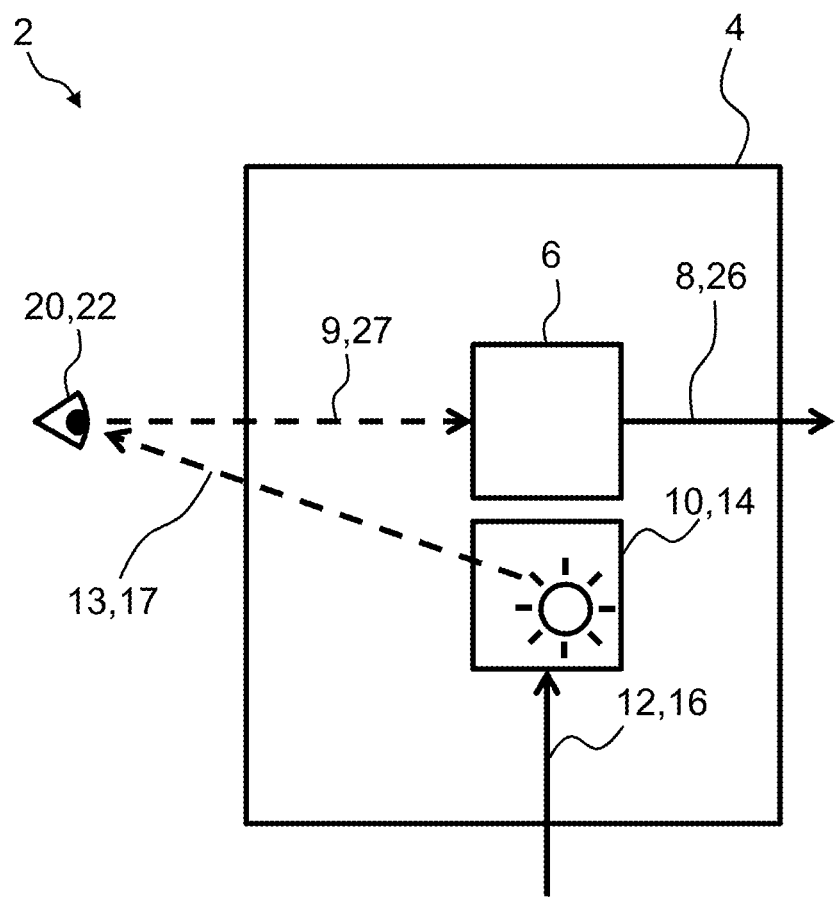
FIG. 1 schematically illustrates an exemplary head mountable device.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout, the same reference numerals are used for identical or corresponding parts.

FIG. 1 schematically illustrates an exemplary head mountable device 2 for measuring eye movement. The head mountable device 2 comprises a frame 4, a camera system 6, and a first liquid crystal display (LCD) shutter 10. In the depicted example, the camera system 6 and the first LCD shutter 10 are mounted on the frame 4.

Figure 7:
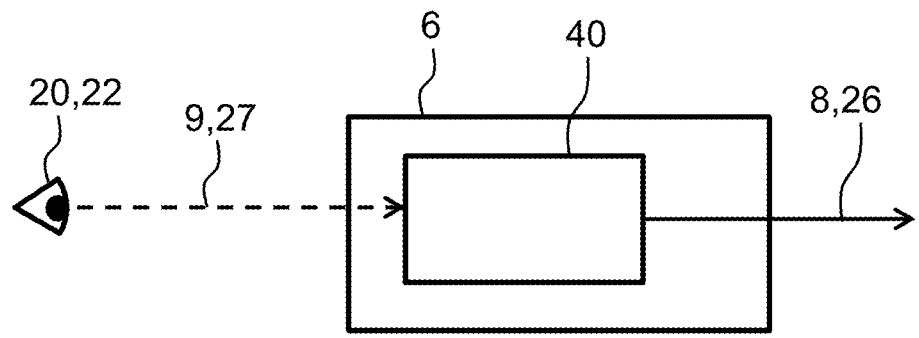
Figure 8:
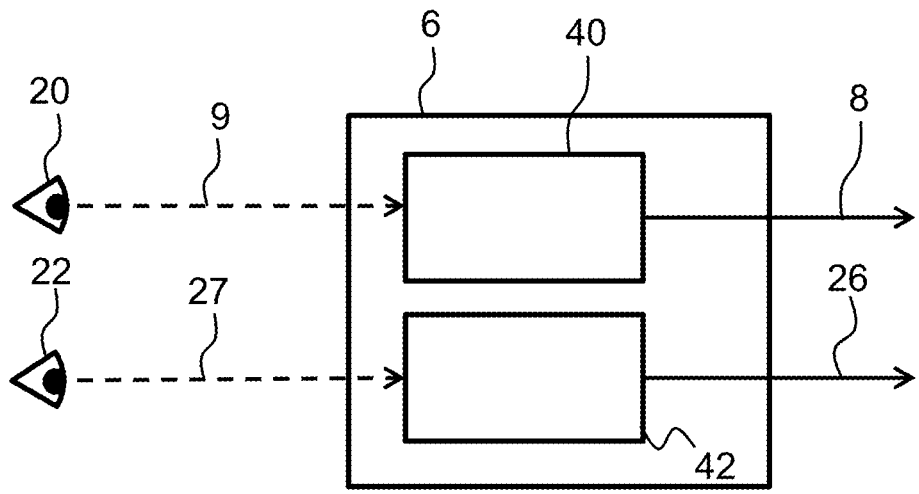

The camera system 6 comprises a first camera (FIGS. 7 and 8). The camera system 6 is configured to obtain a first set of images 8 of a first eye 20 of a user. Alternatively or additionally, the camera system 6 may be configured to obtain a second set of images 26 of a second eye 22 of the user. The camera system 6 detects images 9 of the first eye 20 and converts the images 9 of the first eye 20 to the first set of images 8 of the first eye 20. Alternatively or additionally, the camera system 6 detects images 27 of the second eye 22 and converts the images 27 of the second eye 22 to the second set of images 26 of the second eye 22.

The first LCD shutter 10 is configured to control passage of light 13 to at least part of the first eye 20 based on a first control signal 12. The first LCD shutter 10 is configured to operate in a first primary mode and a first secondary mode. Passage of light 13 through the first LCD shutter 10 in the first secondary mode is restricted relative to the first primary mode. For example, the first LCD shutter 10 may allow passage of light 13 when operating in the first primary mode, and block passage of light 13 when operating in the first secondary mode.

Alternatively or additionally the head mountable device 2 may comprise a second LCD shutter 14. The second LCD shutter 14 is configured to control passage of light 17 to at least part of the second eye 22 based on a second control signal 16. The second LCD shutter 14 is configured to operate in a second primary mode and a second secondary mode. Passage of light 17 through the second LCD shutter 14 in the second secondary mode is restricted relative to the second primary mode. For example, the second LCD shutter 14 may allow passage of light 17 when operating in the second primary mode, and block passage of light 17 when operating in the second secondary mode.

Figure 2:
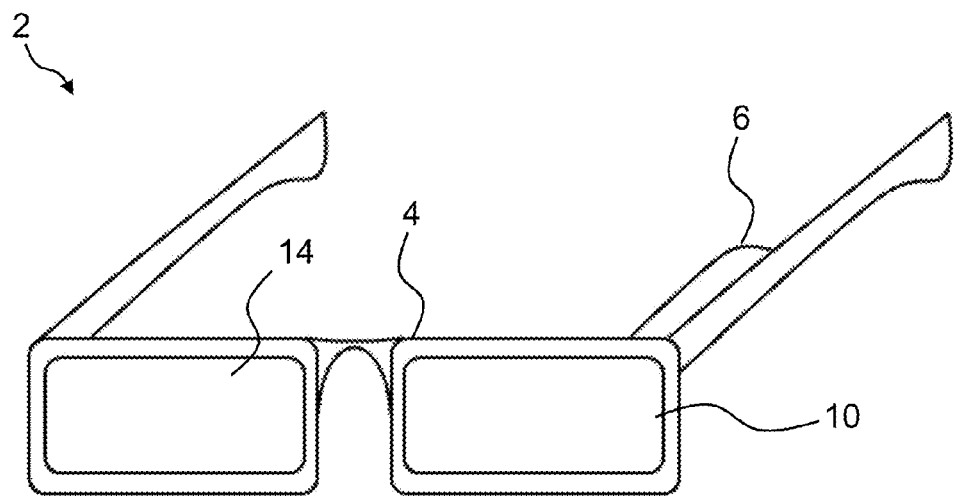
FIG. 2 schematically illustrates an exemplary head mountable device operating in a primary mode, FIG. 3 schematically illustrates an exemplary head mountable device operating in a secondary mode, FIG. 4 schematically illustrates an exemplary head mountable device, FIG. 5 schematically illustrates an exemplary head mountable device, FIG. 6 schematically illustrates an exemplary head mountable device, FIG. 7 schematically illustrates an exemplary camera system, FIG. 8 schematically illustrates an exemplary camera system, FIG. 9 schematically illustrates an exemplary head mountable device, FIG. 10 schematically illustrates an exemplary interface.

FIG. 2 schematically illustrates an exemplary head mountable device 2, wherein a first LCD shutter 10 is operating in a first primary mode, wherein passage of light 13 through the first LCD shutter 10 is allowed. Furthermore a second LCD shutter 14 is operating in a second primary mode, wherein passage of light 17 through the second LCD shutter 14 is allowed.

Figure 3:
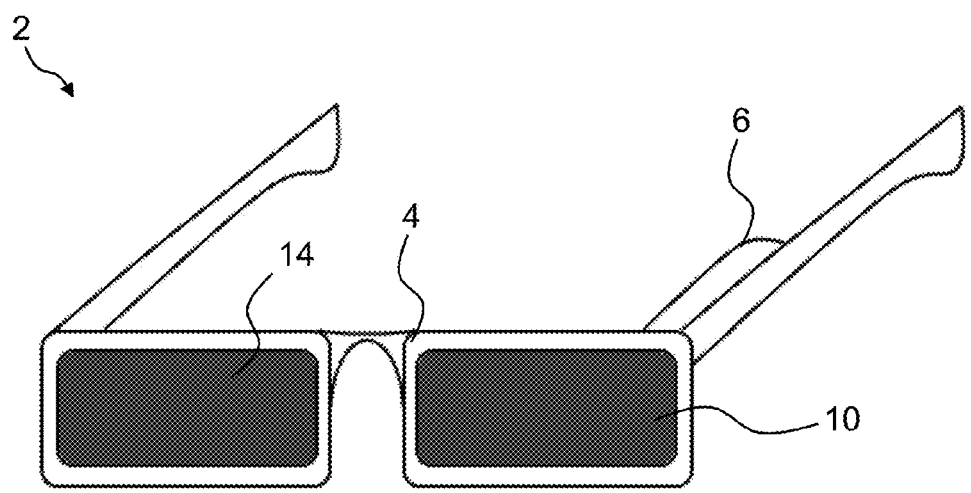

FIG. 3 schematically illustrates an exemplary head mountable device 2, wherein a first LCD shutter is operating in a first secondary mode, wherein passage of light 13 through the first LCD shutter 10 is restricted relative to the first primary mode as illustrated in FIG. 2. Furthermore a second LCD shutter 14 is operating in a second primary mode, wherein passage of light 17 through the second LCD shutter 14 is restricted relative to the second primary mode as illustrated in FIG. 2.

FIGS. 2 and 3 illustrates examples wherein a first LCD shutter 10 and a second LCD shutter 14 are operating concurrently in a primary mode (FIG. 2) or in a secondary mode (FIG. 3). However, it is emphasized that the first LCD shutter 10 and the second LCD shutter 14 may operate independently. For example, the first LCD shutter 10 may be operating in the first primary mode while the second LCD shutter 14 is operating in the second primary mode.

Figure 4:
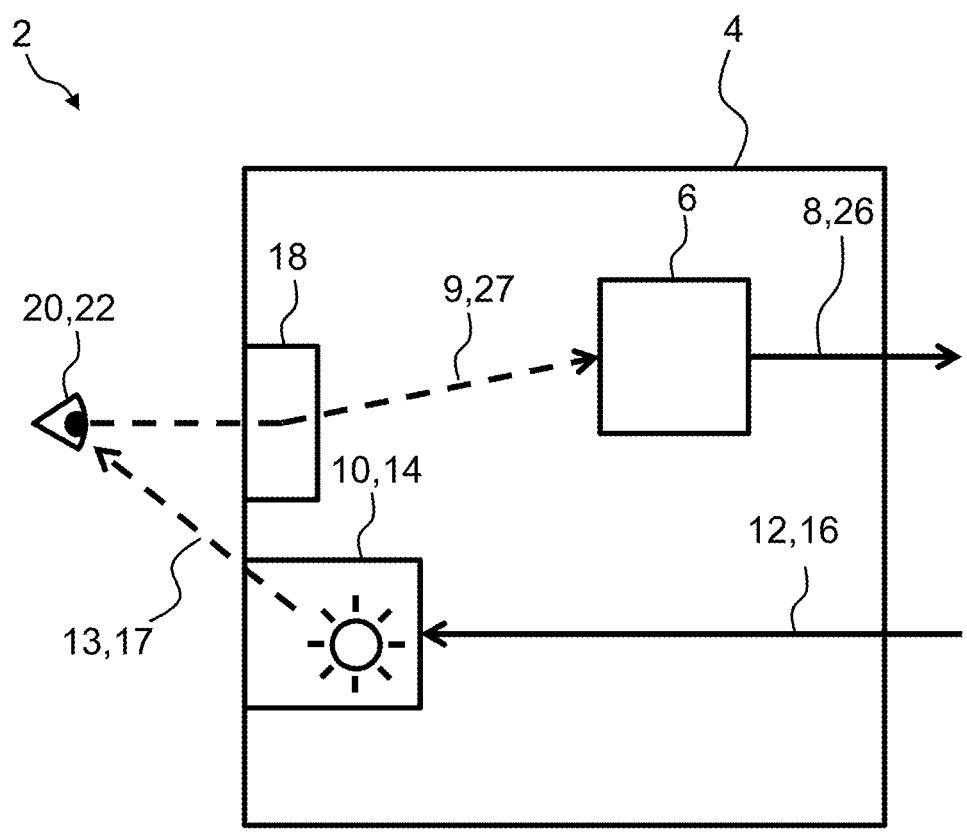

FIG. 4 schematically illustrates an exemplary head mountable device 2 comprising a first mirror 18. The first mirror 18 is configured for mirroring images 9 of the first eye 20 towards the camera system 6. The first mirror 18 may be configured for mirroring images 9 of the first eye 20 towards a first camera of the camera system 6. Alternatively or additionally, the first mirror 18 is configured for mirroring images 27 of the second eye 22 towards the camera system 6. The first mirror 18 may be configured for mirroring images 27 of the second eye 22 towards the first camera and/or a second camera of the camera system 6.

The head mountable device 2 may further comprise a second mirror (not shown), wherein the second mirror is configured for mirroring images 27 of the second eye 22 towards the camera system 6. The second mirror may be configured for mirroring images 27 of the second eye 22 towards the first camera and/or the second camera of the camera system 6.

Figure 5:
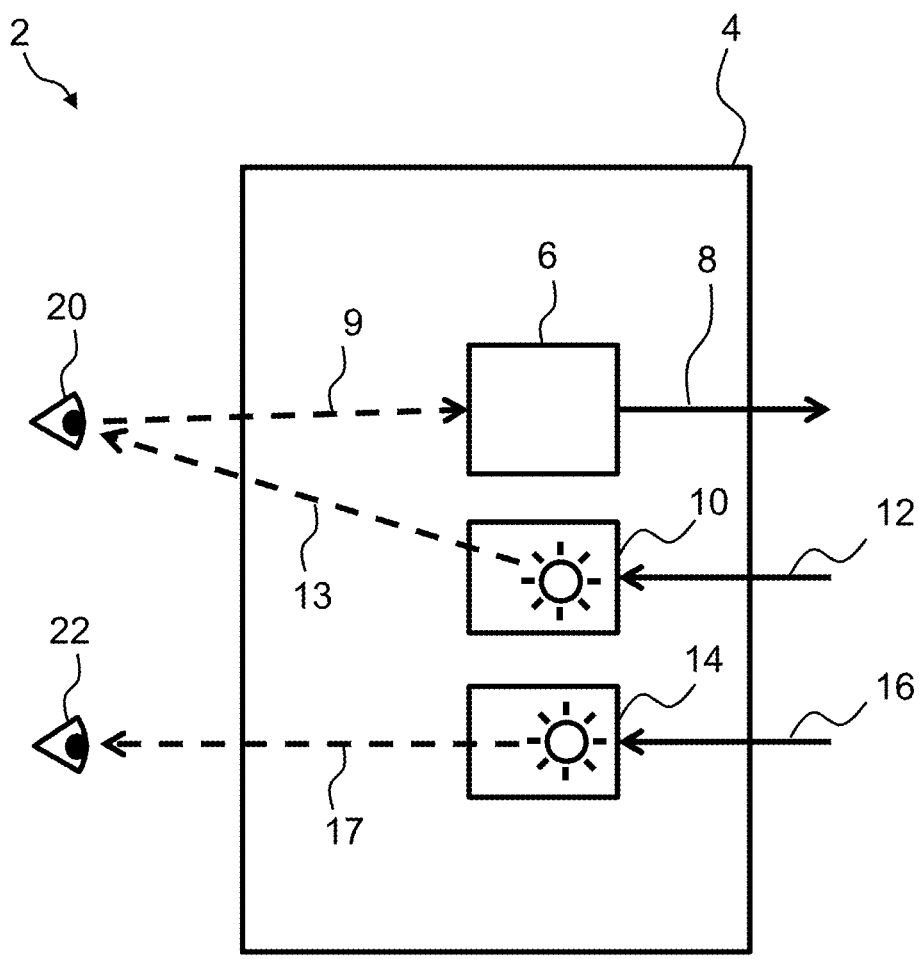

FIG. 5 schematically illustrates an exemplary head mountable device 2 for measuring eye movement. The head mountable device 2 comprises a frame 4, a camera system 6, a first liquid crystal display (LCD) shutter 10, and a second liquid crystal display (LCD) shutter 14. In the depicted example, the camera system 6, the first LCD shutter 10, and the second LCD shutter 14 are mounted on the frame 4.

The camera system 6 is configured to obtain a first set of images 8 of a first eye 20 of a user. The camera system 6 detects images 9 of the first eye 20 and converts the images 9 of the first eye 20 to the first set of images 8 of the first eye 20.

The first LCD shutter 10 is configured to control passage of light 13 to at least part of the first eye 20 based on a first control signal 12. The first LCD shutter 10 is configured to operate in a first primary mode and a first secondary mode. Passage of light 13 through the first LCD shutter 10 in the first secondary mode is restricted relative to the first primary mode.

The second LCD shutter 14 is configured to control passage of light 17 to at least part of the second eye 22 based on a second control signal 16. The second LCD shutter 14 is configured to operate in a second primary mode and a second secondary mode. Passage of light 17 through the second LCD shutter 14 in the second secondary mode is restricted relative to the second primary mode.

Figure 6:
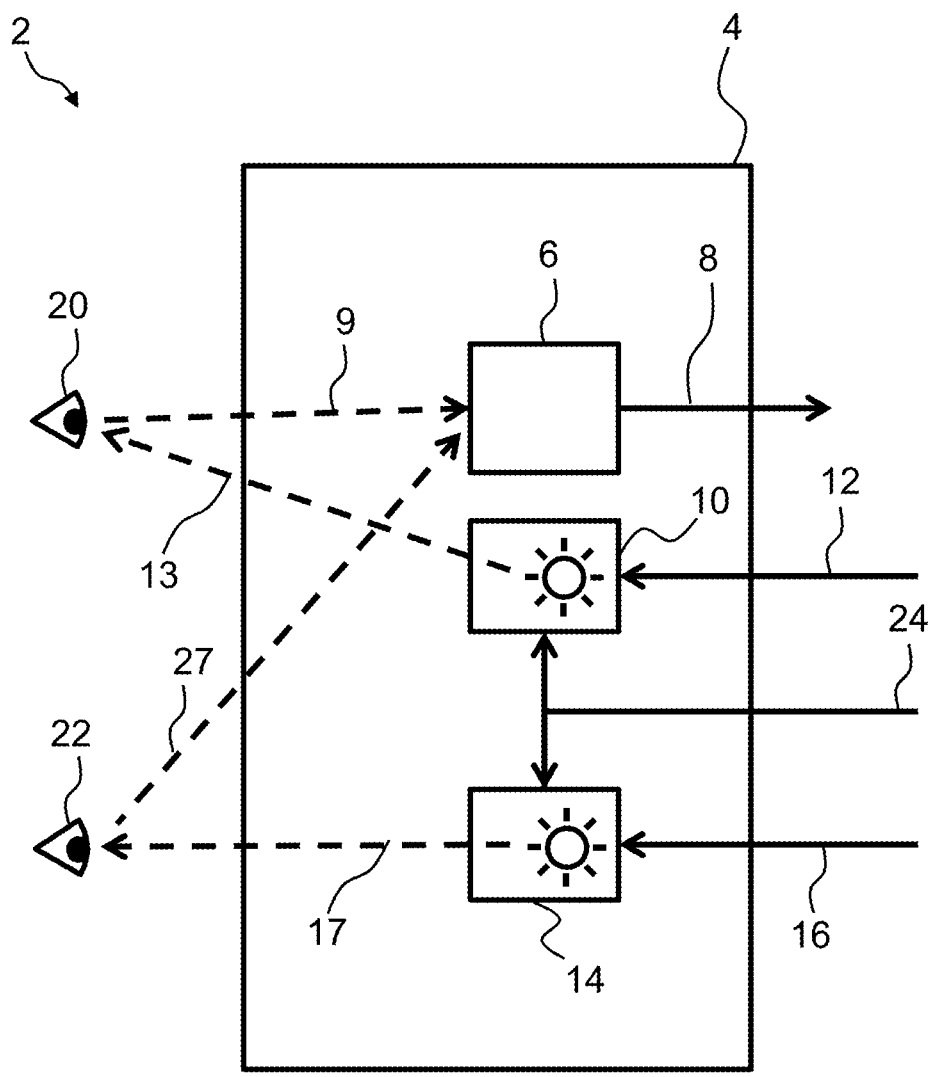

FIG. 6 schematically illustrates an exemplary head mountable device 2 comprising the same features as the exemplary head mountable device as depicted in FIG. 5. However, in FIG. 6, the first LCD shutter 10 is configured to control passage of light 13 to at least part of the first eye 20 based on the first control signal 12 and a common control signal 24. Furthermore, the second LCD shutter 14 is configured to control passage of light 17 to at least part of the second eye 22 based on the second control signal 16 and the common control signal 24. The first control signal 12 and/or the second control signal 16 and/or the common control signal 24 may be alternating current (AC) signals and/or bipolar square wave voltage signals. The first LCD shutter 10 may be configured to operate in the first primary mode when the first control signal 12 and the common control signal 24 are in phase. Conversely, the first LCD shutter 10 may be configured to operate in the first secondary mode when the first control signal 12 and the common control signal 24 are out of phase, e.g. when the first control signal 12 and the common control signal 24 are 180 degrees out of phase. The second LCD shutter 14 may be configured to operate in the second primary mode when the second control signal 16 and the common control signal 24 are in phase. Conversely, the second LCD shutter 14 may be configured to operate in the second secondary mode when the second control signal 16 and the common control signal 24 are out of phase, e.g. when the second control signal 16 and the common control signal 24 are 180 degrees out of phase.

Furthermore, FIG. 6 illustrates an exemplary head mountable device 2, wherein the camera system 6 is configured to obtain a second set of images 26 of a second eye of the user. The camera system 6 is configured to obtain a first set of images 8 of a first eye 20 of a user, and the camera system 6 is configured to obtain a second set of images 26 of a second eye 22 of the user. The camera system 6 detects images 9 of the first eye 20 and converts the images 9 of the first eye 20 to the first set of images 8 of the first eye 20. The camera system 6 detects images 27 of the second eye 22 and converts the images 27 of the second eye 22 to the second set of images 26 of the second eye 22.

FIG. 7 schematically illustrates an exemplary camera system 6 for a head mountable device 2. The camera system 6 comprises a first camera 40. The first camera 40 detects images 9 of a first eye 20 of a user and converts the images 9 of the first eye 20 to a first set of images 8 of the first eye 20. The first camera 40 converts the images 9 of the first eye 20 to a first set of images 8 of the first eye 20 with a first frame rate and a first resolution. Alternatively and/or additionally, the first camera 40 detects images 27 of a second eye 22 of the user and converts the images 27 of the second eye 22 to a second set of images 26 of the second eye 22. The first camera 40 converts the images 27 of the second eye 22 to a second set of images 26 of the second eye 22 with a second frame rate and a second resolution.

FIG. 8 schematically illustrates an exemplary camera system 6 for a head mountable device 2. The camera system 6 of FIG. 8 comprises a first camera 40 and a second camera 42. The first camera 40 detects images 9 of a first eye 20 and converts the images 9 of the first eye 20 to a first set of images 8 of the first eye 20. The first camera converts the images 9 of the first eye 20 to a first set of images 8 of the first eye 20 with a first frame rate and a first resolution. The second camera 42 detects images 27 of a second eye 22 and converts the images 27 of the second eye 22 to a second set of images 26 of the second eye 22. The second camera 42 converts the images 27 of the second eye 22 to a second set of images 26 of the second eye 22 with a second frame rate and a second resolution.

In relation to any of FIGS. 7 and 8, the first camera 40 and/or the second camera 42 may be adapted to enable detection of eye saccades of the first eye 20 and/or second eye 30. For example, the first frame rate and/or the second frame rate may be higher than 125 fps. The first camera 40 and/or the second camera 42 may be able to detect electromagnetic radiation such as infrared radiation (IR), laser light, and/or colored visible light, e.g. red, blue, green, and/or orange visible light. The first camera 40 and/or the second camera 42 may be able to detect electromagnetic radiation of a first light source (not shown).

Figure 9:
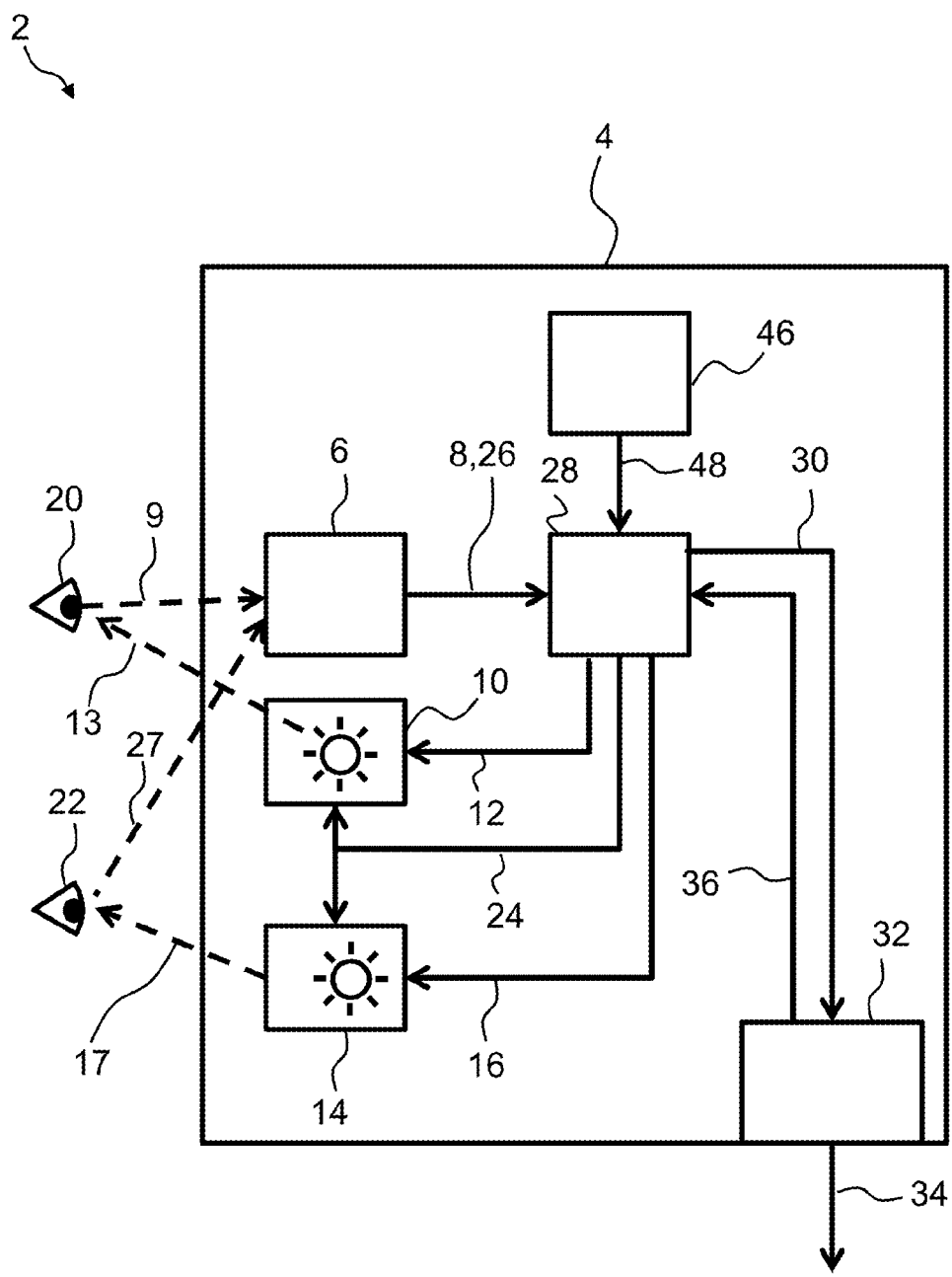

FIG. 9 schematically illustrates an exemplary head mountable device 2, further comprising a number of additional features, which individually and/or in combination may be added to the head mountable device 2 described in relation to any of the preceding figures. The head mountable device 2 of FIG. 9 further comprises a processing unit 28, an interface 32, and a motion sensor 46.

The frame 4 comprises the camera system 6, the first LCD shutter 10, the second LCD shutter 14, the processing unit 28, the interface 32, and the first motion sensor 46. In other exemplary head mountable devices (not shown), the frame 4 may comprise one or more of the camera system 6, the first LCD shutter 10, the second LCD shutter 14, the processing unit 28, the interface 32, and the first motion sensor 46.

The processing unit 28 may be configured to process the first set of images 8 and/or the second set of images 26 and provide a processing unit output 30. The processing unit output 30 may be based on the first set of images 8 and/or the processing unit output 30 may be based on the second set of images 26. Furthermore, the first control signal 12 and the second control signal 16 and the common control signal 24 is controlled by the processing unit 28. In alternative exemplary head mountable devices, the processing unit 28 may control one or more of the first control signal 12 and the second control signal 16 and the common control signal 24.

The interface 32 provides a device output 34. The device output 34 may be based on the first set of images 8 and/or the second set of images 26. In the depicted example, the device output 34 is based on the processing unit output 30 which is based on the first set of images 8 and/or the second set of images 26.

In the depicted example, the interface 32 provides a processing unit control signal 36. However, in other exemplary head mountable devices, the provision of a processing unit control signal 36 may be omitted. The processing unit control signal 36 may allow user control of the processing unit 28 and/or the head mountable device 2 via an input device, such as a user interface, of the interface 32.

The motion sensor 46 is configured to detect movement of the head mountable device 2. The processing unit 28 is connected to the motion sensor 46. The motion sensor 46 provides a sensor output 48. The processing unit 28 is configured to process the sensor output 48 from the first motion sensor 46, and the processing unit output 30 may be based on the sensor output 48. The motion sensor 46 may comprise one or more gyroscope(s) and/or one or more accelerometer(s).

The processing unit 28 may compress and/or reduce the amount of data in the processing unit output 30. For example, in order for the interface 32 to transmit the device output 34, or a part of the device output 34, wirelessly, without substantial delay e.g. a delay of the order of 10 ms, the processing unit output 30 may be compressed and/or reduced. For example, the processing unit output 30 may comprise a first secondary set of images with a first secondary frame rate and a first secondary resolution, wherein the first secondary frame rate is smaller than the first frame rate and/or the first secondary resolution is smaller than the first resolution. Alternatively and/or additionally the processing unit output 30 may comprise a second secondary set of images with a second secondary frame rate and a second secondary resolution, wherein the second secondary frame rate is smaller than the second frame rate and/or the second secondary resolution is smaller than the second resolution.

Additionally and/or alternatively, the processing unit 28 may be configured to compress an initial processing unit output based on the first set of images 8 and/or the second set of images 26, wherein the size of the processing unit output 30 is below 20%, such as 10%, such as 5% of the size of the initial processing unit output.

The processing unit output 30 and/or the device output 34 may be indicative of one or more parameters of the user, such as an ophthalmologic parameter, a vestibular parameter, and/or a neurologic parameter.

Figure 10:
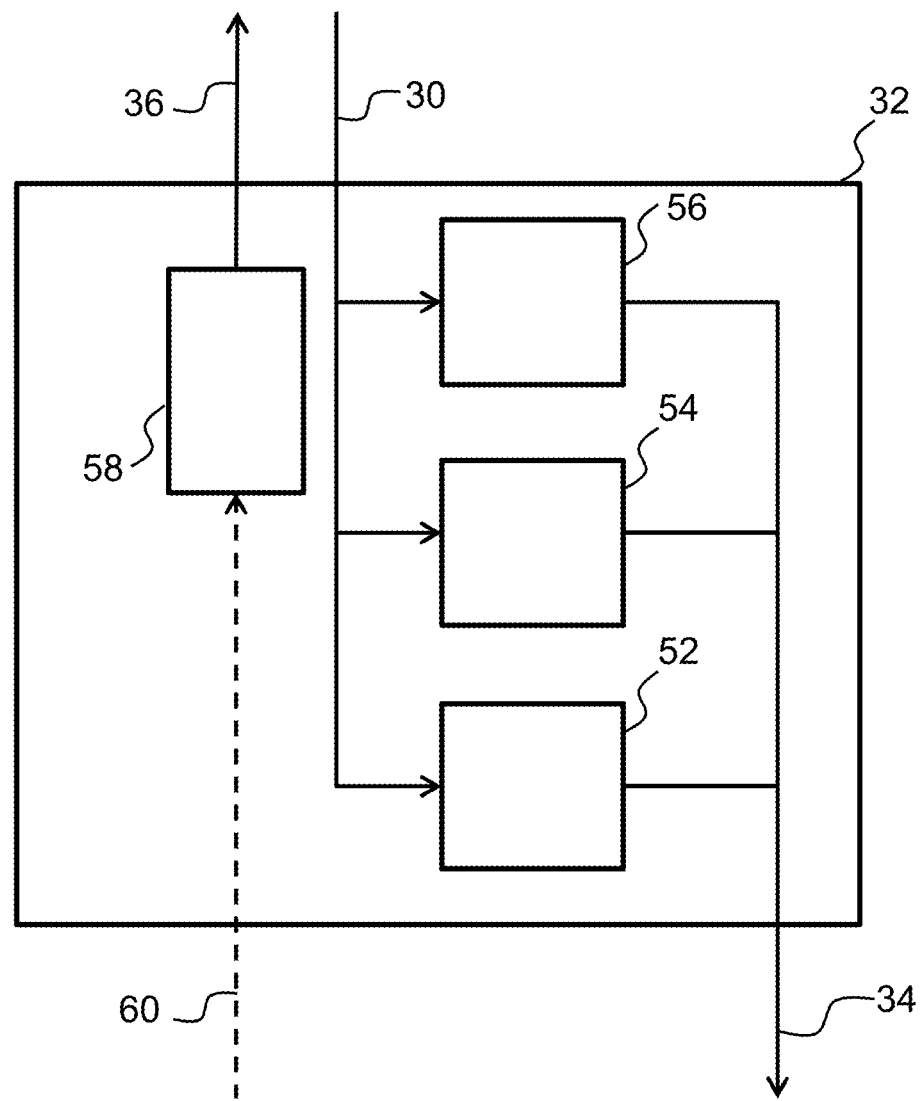

FIG. 10 schematically illustrates an exemplary interface 32. The interface 32 comprises a wireless transmitter unit 52, a first display 54, a speaker 56, and/or an input device 58. The interface 32 may in alternative configurations (not shown) comprise one or more of the wireless transmitter unit 52, the first display 54, the speaker 56 and the input device 58.

The wireless transmitter unit 52 receives the processing unit output 30, or part of the processing unit output 30, and transmits the device output 34, or a part of the device output 34, wirelessly to a wireless receiver (not shown). The wireless transmitter unit 52 may be a Bluetooth transmitter, a WiFi transmitter, a 3G transmitter and/or a 4G transmitter. The wireless transmitter unit 52 may further be configured to transmit the device output 34, or a part of the device output 34, with a low latency to enable live preview of the device output 34 in an external display. The latency may be less than 40 ms such as less than 20 ms such as less than 10 ms.

The first display 54 receives the processing unit output 30, or part of the processing unit output 30, and visually presents the device output 34, or a part of the device output 34, to a user or an operator of the device. The first display 54 may be an organic light emitting diode (OLED), an OLED display, a light emitting diode (LED), an LED display, and/or an e-ink display.

The speaker 56 receives the processing unit output 30, or part of the processing unit output 30, and audiologically, by means of sounds, presents the device output 34, or a part of the device output 34, to a user or an operator of the device.

The input device 58 enables control of the head mountable device 2. User interaction 60 is detected by the input device 58, and the input device 58 provides a control signal 36 to the processing unit 12. The input device 58 may comprise a push button, a switch, and/or a touch display.

The device output 34 may be indicative of a positive/negative result of a test. For example, the device output 34 may comprise lighting up the first display 54 in a red colour if the test result is negative, and/or lighting up the first display 54 in a green colour if the test result is positive. For example, the device output 34 is indicative of an ophthalmologic parameter of the user, the device output 34 is indicative of a vestibular parameter of the user, and/or the device output 34 is indicative of a neurologic parameter of the user.

The device output 34 may comprise a plurality of output images based on the first set of images 8 and/or based on the second set of images 26. For example, the device output 34 may provide a live preview of the images 9, 27 of the first eye 20 and/or the second eye 22. The live preview may be transmitted wirelessly via the wireless transmitter 52 to an external display, e.g. a display of an external device, such as a tablet computer, a smart phone, or a laptop.

Figure 11:
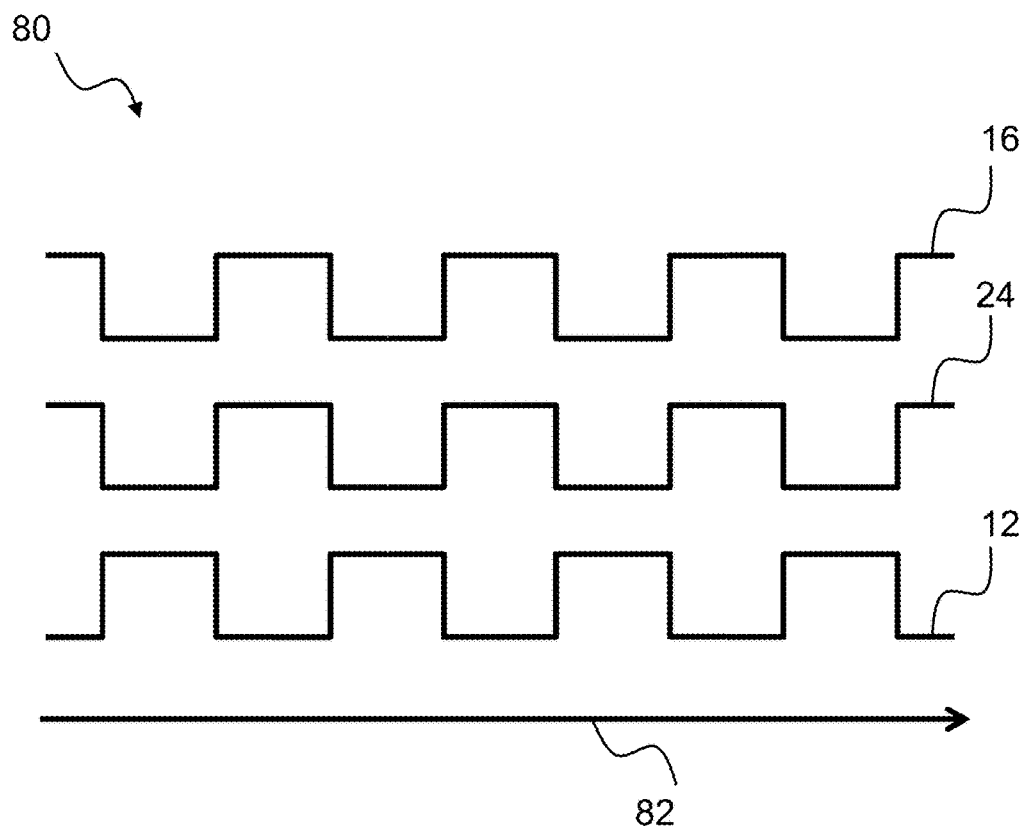
FIG. 11 illustrates exemplary control signals for a head mountable device

FIG. 11 illustrates voltage traces 80 of exemplary control signals 12, 16, 24 for a head mountable device 2. The voltage traces 80 of the control signals 12, 16, 24 are shown on a time axis 82. In the depicted example, the control signals 12, 16, 24 are bipolar square wave signals. The control signals shown are the first control signal 12 for the first LCD shutter 10, the second control signal 16 for the second LCD shutter 14, and the common control signal 24 for both the first LCD shutter 10 and second LCD shutter 14.

The depicted example shows the first control signal 12 and the common control signal 24 to be 180 degrees out of phase. This generates a voltage difference between the first control signal 12 and the common control signal 24. The voltage difference may result in the first LCD shutter 10 to operate in the first secondary operating mode where passage of light through the first LCD shutter 10 is restricted and/or blocked.

The depicted example shows the second control signal 16 and the common control signal 24 to be in phase. This generates no voltage difference between the second control signal 16 and the common control signal 24. The zero voltage difference may result in the second LCD shutter 14 to operate in the second primary operating mode where passage of light through the second LCD shutter 14 is not restricted and/or blocked, i.e. passage of light through the second LCD shutter 14 is allowed.

Changing the operating modes of the first LCD shutter 10 and/or the second LCD shutter 14 may be achieved by altering the first control signal 12, the common control signal 24, and/or the second control signal 16 to be in phase or 180 degrees out of phase.

In alternative embodiments (not shown), the first control signal 12 and/or the second control signal 16 may be DC signals. However, using AC signals and/or bipolar square wave signals, possible migration of crystals within the LCD shutters 10, 14 will be prevented.

Figure 12:
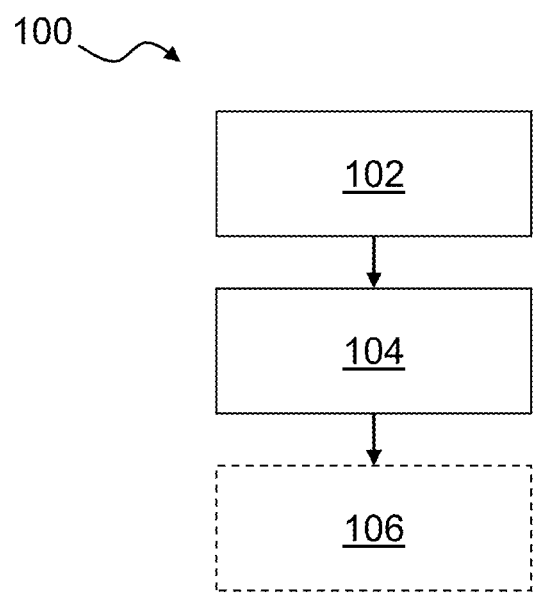
FIG. 12 shows a method for measuring eye movement.

FIG. 12 shows a flow diagram of a method 100 for measuring eye movement. The method 100 may comprise using a head mountable device 2, such as a head mountable device 2 as described in relation to any of the previous figures. The method comprises adjusting 102 passage of light to at least part of a first eye and/or a second eye, and obtaining 104 a first set of images of the first eye and/or a second set of images of the second eye. Optionally, the method may comprise providing 106 a device output based on the first set of images and/or the second set of images.

Adjusting 102 passage of light to at least part of the first eye and/or a second eye may be achieved by operation of the first LCD shutter 10 and/or second LCD shutter 14 of the head mountable device 2.

Obtaining 104 the first set of images and/or the second set of images may be achieved by the camera system 6 of the head mountable device 2. The first set of images and/or the second set on images may be obtained with a respective first frame rate and/or second frame rate enabling detection of eye saccades of the respective first eye and/or second eye, e.g. a first frame rate and/or a second frame rate higher than 125 fps.

The device output provided 106 may be indicative of one or more parameters of the user, e.g. a vestibular parameter of the user, an ophthalmologic parameter of the user, and/or a neurologic parameter of the user. The device output may further be indicative of a test result, such as a vestibular test, an ophthalmologic test and/or a neurologic test. The device output may be provided 106 via an audiologic output, a visual output, and/or wireless transmission to an external device.

The method 100 may furthermore comprise mounting (not shown) the head mountable device 2 to a head of the user, and/or detecting (not shown) movement of the head mountable device 2.

Mounting of the head mountable device 2 to a head of the user may be performed by an operator, and may involve fastening the head mountable device 2 to the head of the user to avoid movement of the head mountable device 2 relative to the head of the user. If the device is tightly fixed to the head, moving the head of the user involves movement of the head mountable device 2. Thus, the movement of the device 2 corresponds to the movement of the head of the user. Detecting of the movement of the head mountable device is therefore indicative of the moving of the head of the user.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Embodiments and aspects are disclosed in the following items:

Item 1. A head mountable device for measuring eye movement, the head mountable device comprising:
a frame;
a camera system comprising a first camera, wherein the camera system is configured to obtain a first set of images of a first eye of a user;
a first liquid crystal display (LCD) shutter configured to control passage of light to at least part of the first eye based on a first control signal, the first LCD shutter is configured to operate in a first primary mode and a first secondary mode, where passage of light through the first LCD shutter in the first secondary mode is restricted relative to the first primary mode.

Item 2. Head mountable device according to item 1, wherein the head mountable device comprises a first mirror for mirroring images of the first eye towards the first camera.

Item 3. Head mountable device according to any of items 1-2, wherein the head mountable device comprises a second liquid crystal display (LCD) shutter configured to control passage of light to at least part of a second eye of the user based on a second control signal, the second LCD shutter is configured to operate in a second primary mode and a second secondary mode, where passage of light through the second LCD shutter in the second secondary mode is restricted relative to the second primary mode.

Item 4. Head mountable device according to item 3, wherein the first LCD shutter is configured to control passage of light through the first LCD shutter based on the first control signal and a common control signal, and wherein the second LCD shutter is configured to control passage of light through the second LCD shutter based on the second control signal and the common control signal.

Item 5. Head mountable device according to item 4, wherein the first control signal, the second control signal, and/or the common control signal are alternating current (AC) signals and/or bipolar square wave voltage signals.

Item 6. Head mountable device according to any of the preceding items, wherein voltage of the first control signal, the second control signal, and/or the common control signal is in the range from 2 to 14 volts, such as 5 volts or such as 10 volts.

Item 7. Head mountable device according to any of the preceding items, wherein the camera system is configured to obtain a second set of images of a second eye of the user.

Item 8. Head mountable device according to item 7, wherein the camera system comprises a second camera configured to obtain the second set of images.

Item 9. Head mountable device according to any of the preceding items, wherein the first set of images is configured to be obtained with a first frame rate, wherein the first frame rate is selected such as to enable detection of eye saccades of the first eye.

Item 10. Head mountable device according to any of the preceding items, wherein the head mountable device comprises a processing unit configured to process the first set of images and providing a processing unit output based on the first set of images.

Item 11. Head mountable device according to item 10, wherein the first control signal, the second control signal, and/or the common control signal are controlled by the processing unit.

Item 12. Head mountable device according to any of the preceding items, wherein the head mountable device comprises an interface for providing a device output based on the first set of images.

Item 13. Head mountable device according to any of the preceding items, wherein the frame accommodates the camera system and the first LCD shutter.

Item 14. Method for measuring eye movement of a user using a head mountable device comprising a frame, a camera system comprising a first camera, and a first liquid crystal display (LCD) shutter configured to control passage of light to at least part of a first eye of a user based on a first control signal, the first LCD shutter is configured to operate in a first primary mode and a first secondary mode, where passage of light through the first LCD shutter in the first secondary mode is restricted relative to the first primary mode, the method comprising:
adjusting passage of light to at least part of the first eye by operation of the first LCD shutter; and
obtaining a first set of images of the first eye by the camera system.

Item 15. Method according to item 14, wherein the method comprises providing a device output based on the first set of images.

LIST OF REFERENCES 2 head mountable device
4 frame
6 camera system
8 first set of images
9 image(s) of first eye
10 first LCD shutter
12 first control signal
13 light through first LCD shutter
14 second LCD shutter
16 second control signal
17 light through second LCD shutter
18 first mirror
20 first eye
22 second eye
24 common control signal
26 second set of images
27 image(s) of second eye
28 processing unit
30 processing unit output
32 interface
34 device output
36 processing unit control signal
40 first camera
42 second camera
46 motion sensor
48 sensor output
52 wireless transmitter unit
54 first display
56 speaker
58 input device
60 user interaction
80 control signals
82 time axis
100 method
102 adjusting passage of light
104 obtaining first set of images
106 providing device output

The invention claimed is:

1. A head mountable device for measuring eye movement, the head mountable device comprising:
   a frame;
   a camera system comprising a first camera, wherein the camera system is coupled to the frame, and is configured to provide a first set of images of a first eye of a user to a processing unit that is configured to process the first set of images of the first eye; and
   a first liquid crystal display (LCD) shutter configured to control passage of light to the first eye based at least in part on a first control signal, the first LCD shutter is configured to operate in a first primary mode and a first secondary mode, wherein the first LCD shutter is configured to allow less light to reach the first eye in the first secondary mode than in the first primary mode.

2. The head mountable device according to claim 1, further comprising a first mirror for mirroring images of the first eye towards the first camera.

3. The head mountable device according to claim 1, further comprising a second liquid crystal display (LCD) shutter configured to control passage of light to a second eye of the user based at least in part on a second control signal, the second LCD shutter being configured to operate in a second primary mode and a second secondary mode, wherein the second LCD shutter is configured to allow less light to reach the second eye in the second secondary mode than in the second primary mode.

4. A head mountable device for measuring eye movement, the head mountable device comprising:
   a frame;
   a camera system comprising a first camera, wherein the camera system is coupled to the frame, and is configured to provide a first set of images of a first eye of a user; and
   a first liquid crystal display (LCD) shutter configured to control passage of light to the first eye based at least in part on a first control signal, the first LCD shutter is configured to operate in a first primary mode and a first secondary mode, wherein the first LCD shutter is configured to allow less light to reach the first eye in the first secondary mode than in the first primary mode;
   a second liquid crystal display (LCD) shutter configured to control passage of light to a second eye of the user based at least in part on a second control signal, the second LCD shutter being configured to operate in a second primary mode and a second secondary mode, wherein the second LCD shutter is configured to allow less light to reach the second eye in the second secondary mode than in the second primary mode;
   wherein the first LCD shutter is configured to control passage of light through the first LCD shutter based on the first control signal and a common control signal, and wherein the second LCD shutter is configured to control passage of light through the second LCD shutter based on the second control signal and the common control signal.

5. The head mountable device according to claim 4, wherein the first control signal, the second control signal, and/or the common control signal comprises alternating current (AC) signal(s) and/or bipolar square wave voltage signal(s).

6. The head mountable device according to claim 4, wherein a voltage of at least one of the first control signal, the second control signal, and the common control signal is anywhere from 2 to 14 volts.

7. The head mountable device according to claim 1, wherein the camera system is configured to provide a second set of images of a second eye of the user.

8. The head mountable device according to claim 7, wherein the camera system comprises a second camera configured to provide the second set of images.

9. The head mountable device according to claim 1, wherein the camera system is configured to provide the first set of images with a first frame rate, the first frame rate being sufficient to enable detection of eye saccades of the first eye.

10. The head mountable device according to claim 1, further comprising the processing unit, wherein the processing unit is configured to provide a processing unit output based on the first set of images.

11. The head mountable device according to claim 10, wherein the first control signal is controlled by the processing unit.

12. The head mountable device according to claim 1, further comprising an interface for providing a device output based on the first set of images.

13. The head mountable device according to claim 1, wherein the frame accommodates the camera system and the first LCD shutter.

14. A method performed by a head mountable device, the head mountable device comprising a frame, a camera system coupled to the frame and comprising a first camera, and a first liquid crystal display (LCD) shutter configured to control passage of light to a first eye of a user based at least in part on a first control signal, the first LCD shutter being configured to operate in a first primary mode and a first secondary mode, wherein the first LCD shutter is configured to allow less light to reach the first eye in the first secondary mode than in the first primary mode, the method comprising:

adjusting passage of light to the first eye by operation of the first LCD shutter; and providing a first set of images of the first eye by the camera system for processing by a processing unit.

15. The method according to claim 14, further comprising providing a device output based on the first set of images.

16. The head mountable device according to claim 1, further comprising the processing unit, wherein the processing unit is located at the frame.

* * * * *